(12) United States Patent
Harms et al.

(10) Patent No.: US 10,286,150 B2
(45) Date of Patent: May 14, 2019

(54) DOSE BUTTON FOR A DRUG DELIVERY DEVICE AND METHOD FOR MANUFACTURING A DOSE BUTTON

(76) Inventors: Michael Harms, Frankfurt am Main (DE); Steffen Raab, Frankfurt am Main (DE); Udo Stauder, Frankfurt am Main (DE); Richard James Vincent Avery, Gloucestershire (GB); Christopher Nigel Langley, Warwickshire (GB); James Alexander Senior, Warwickshire (GB); James Alexander Davies, Warwickshire (GB)

(*) Notice: Subject to any disclaimer, the term of this patent is extended or adjusted under 35 U.S.C. 154(b) by 1180 days.

(21) Appl. No.: 13/254,470

(22) PCT Filed: Mar. 31, 2010

(86) PCT No.: PCT/EP2010/054352
§ 371 (c)(1),
(2), (4) Date: Feb. 29, 2012

(87) PCT Pub. No.: WO2010/112565
PCT Pub. Date: Oct. 7, 2010

(65) Prior Publication Data
US 2012/0165741 A1    Jun. 28, 2012

Related U.S. Application Data

(60) Provisional application No. 61/169,880, filed on Apr. 16, 2009.

(30) Foreign Application Priority Data

Mar. 31, 2009 (EP) ..................... 09004674

(51) Int. Cl.
*A61M 5/20* (2006.01)
*A61M 5/00* (2006.01)
*A61M 37/00* (2006.01)

(52) U.S. Cl.
CPC ............. *A61M 5/20* (2013.01); *A61M 5/003* (2013.01); *A61M 37/00* (2013.01);
(Continued)

(58) Field of Classification Search
CPC .. A61M 5/20; A61M 5/003; A61M 2205/582; A61M 2205/584;
(Continued)

(56) References Cited

U.S. PATENT DOCUMENTS

| 533,575 A | 2/1895 | Wilkens |
| 3,343,539 A | 9/1967 | Moorhouse |

(Continued)

FOREIGN PATENT DOCUMENTS

| CA | 2138528 | 12/1998 |
| CA | 2359375 A1 | 7/2000 |

(Continued)

OTHER PUBLICATIONS

Communication pursuant to Article 94/(3) EPC issued in European Patent Application No. 10713891.9 dated Oct. 5, 2017.
(Continued)

*Primary Examiner* — Lauren P Farrar
(74) *Attorney, Agent, or Firm* — McCarter & English, LLP

(57) ABSTRACT

The present invention relates to a drug delivery device (6) comprising a dose button (1). Furthermore it relates to a method for manufacturing a dose button (1) by using a cutting-off process. The aim of the present invention is to minimize the risk of using a drug delivery device (6) containing a wrong drug. By means of tactile features, a drug delivery device (6) is distinguishable from another drug delivery device (6) containing another type of drug. This tactile feature is manufactured by using a dose button (1) out of metal which is milled or lathed.

14 Claims, 3 Drawing Sheets

Figure 1:
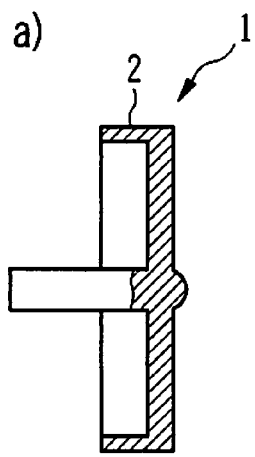
Figure 1:
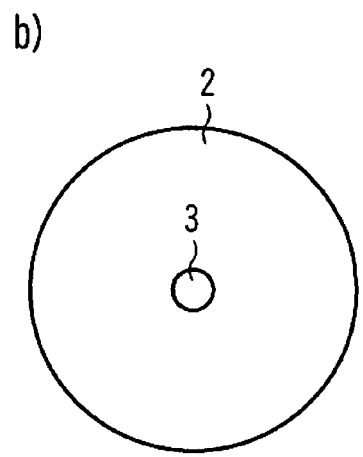
Figure 1:
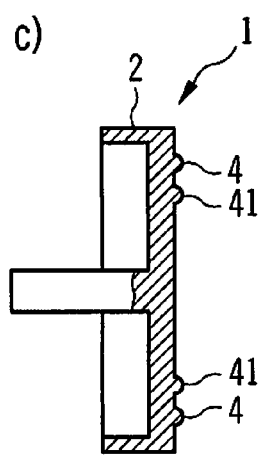
Figure 1:
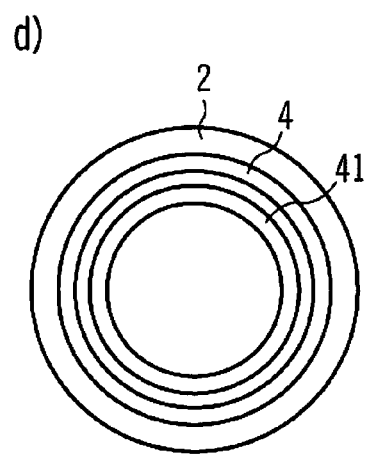
Figure 1:
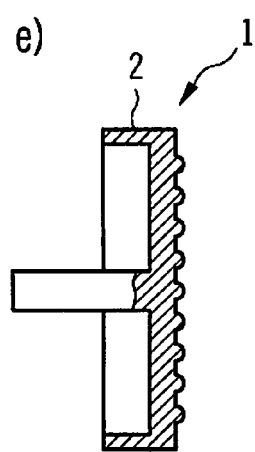
Figure 1:
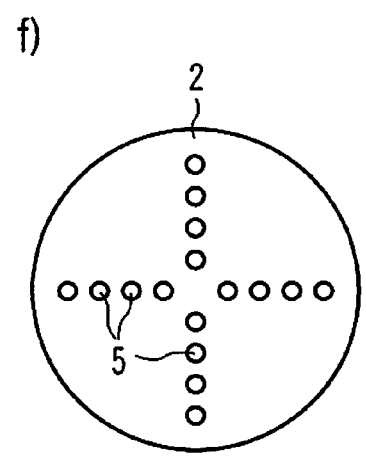

(52) U.S. Cl.
CPC . *A61M 2205/582* (2013.01); *A61M 2205/584* (2013.01); *A61M 2205/6036* (2013.01); *A61M 2205/6081* (2013.01); *Y10T 82/10* (2015.01); *Y10T 82/16016* (2015.01); *Y10T 409/303752* (2015.01)

(58) Field of Classification Search
CPC .. A61M 2205/6036; A61M 2205/6081; A61M 5/31533; A61M 5/31565; Y10T 409/303752; Y10T 82/10; Y10T 82/16016; Y10T 37/00
See application file for complete search history.

(56) References Cited

U.S. PATENT DOCUMENTS

| | | | |
|---|---|---|---|
| 3,878,846 A | | 4/1975 | Rimbaud |
| 3,958,570 A | * | 5/1976 | Vogelman ............... A61M 5/24 604/206 |
| 4,610,666 A | * | 9/1986 | Pizzino ................... A61M 5/19 604/191 |
| 4,865,591 A | | 9/1989 | Sams |
| 5,092,842 A | | 3/1992 | Bechtold et al. |
| 5,226,895 A | | 7/1993 | Harris |
| 5,226,896 A | | 7/1993 | Harris |
| 5,279,586 A | | 1/1994 | Balkwin |
| 5,304,152 A | | 4/1994 | Sams |
| 5,320,609 A | | 6/1994 | Haber et al. |
| 5,354,287 A | * | 10/1994 | Wacks .................... A61M 5/24 128/DIG. 1 |
| 5,378,233 A | | 1/1995 | Haber et al. |
| 5,383,865 A | | 1/1995 | Michael |
| 5,391,157 A | | 2/1995 | Harris et al. |
| 5,480,387 A | | 1/1996 | Gabriel et al. |
| 5,505,704 A | | 4/1996 | Pawelka et al. |
| 5,542,920 A | * | 8/1996 | Cherif Cheikh .. A61M 37/0069 604/309 |
| 5,582,598 A | | 12/1996 | Chanoch |
| 5,626,566 A | | 5/1997 | Petersen et al. |
| 5,674,204 A | | 10/1997 | Chanoch |
| 5,688,251 A | | 11/1997 | Chanoch |
| 5,807,346 A | | 9/1998 | Frezza |
| 5,820,602 A | | 10/1998 | Kovelman et al. |
| 5,851,079 A | | 12/1998 | Horstman et al. |
| 5,921,966 A | | 7/1999 | Bendek et al. |
| 5,941,394 A | * | 8/1999 | Siegler ...................... A61J 7/04 206/366 |
| 5,957,896 A | | 9/1999 | Bendek et al. |
| 5,961,495 A | | 10/1999 | Walters et al. |
| 6,193,698 B1 | | 2/2001 | Kirchhofer et al. |
| 6,221,046 B1 | | 4/2001 | Burroughs et al. |
| 6,235,004 B1 | | 5/2001 | Steenfeldt-Jensen et al. |
| 6,248,095 B1 | | 6/2001 | Giambattista et al. |
| 6,562,006 B1 | | 5/2003 | Hjertman et al. |
| 6,613,023 B2 | | 9/2003 | Kirchhofer et al. |
| 6,699,224 B2 | | 3/2004 | Kirchhofer et al. |
| 6,899,698 B2 | | 5/2005 | Sams |
| 6,932,794 B2 | | 8/2005 | Giambattista et al. |
| 6,936,032 B1 | | 8/2005 | Bush, Jr. et al. |
| 7,169,132 B2 | | 1/2007 | Bendek et al. |
| 7,241,278 B2 | | 7/2007 | Moller |
| 7,678,084 B2 | | 3/2010 | Judson et al. |
| 7,850,662 B2 | | 12/2010 | Veasey et al. |
| 8,186,233 B2 | | 5/2012 | Joung et al. |
| 2002/0014028 A1 | * | 2/2002 | Campeau ............. G09B 21/003 40/310 |
| 2002/0120235 A1 | | 8/2002 | Enggaard |
| 2004/0089292 A1 | * | 5/2004 | Pollet ................ A61M 15/0025 128/200.23 |
| 2004/0097883 A1 | | 5/2004 | Roe |
| 2004/0210199 A1 | | 10/2004 | Atterbury et al. |
| 2004/0267207 A1 | | 12/2004 | Veasey et al. |
| 2005/0119622 A1 | * | 6/2005 | Temple ...................... A61J 7/04 604/189 |
| 2006/0153693 A1 | | 7/2006 | Fiechter et al. |
| 2007/0016143 A1 | | 1/2007 | Miller et al. |
| 2007/0129687 A1 | | 6/2007 | Marshall et al. |
| 2009/0275916 A1 | | 11/2009 | Harms et al. |

FOREIGN PATENT DOCUMENTS

| | | |
|---|---|---|
| DE | 2915339 A1 | 11/1980 |
| EP | 0496141 A1 | 7/1992 |
| EP | 0554995 A1 | 8/1993 |
| EP | 0897729 A2 | 2/1999 |
| EP | 0937471 A2 | 8/1999 |
| EP | 0937476 A2 | 8/1999 |
| EP | 1776975 A2 | 4/2007 |
| EP | 1923085 A1 | 5/2008 |
| GB | 190226674 | 10/2003 |
| WO | 9324160 A1 | 12/1993 |
| WO | 97/40875 A2 | 11/1997 |
| WO | 9307922 A1 | 4/1999 |
| WO | 9938554 A1 | 8/1999 |
| WO | 9947062 A1 | 9/1999 |
| WO | 0230495 A2 | 4/2002 |
| WO | 02092153 A2 | 11/2002 |
| WO | 03/086511 A1 | 10/2003 |
| WO | 03080160 A1 | 10/2003 |
| WO | 03086511 A1 | 10/2003 |
| WO | 2006084876 A1 | 8/2006 |
| WO | 2007/060156 A1 | 5/2007 |
| WO | 2007060153 A1 | 5/2007 |

OTHER PUBLICATIONS

ISO—International Organization for Standarization, Pen-injectors for medical use, Part 1: Pen-injectors—Requirements and test methds. ISO 11608-1, First Edition, 32 pages, Dec. 15, 2000.

ISO—International Organization for Standarization, Pen-injectors for medical use, Part 2: Needles—Requirements and test methods. ISO 11608-2, First Edition, 18 pages, Dec. 15, 2000.

ISO—International Organization for Standarization, Pen-injectors for medical use, Part 3: Finished cartridges—Requirements and test methods. ISO 11608-3, First Edition, 22 pages, Dec. 15, 2000.

Examination Report issued for India Patent Application No. 7044/CHENP/2011, dispatched Sep. 28, 2018 (5 pages).

* cited by examiner a) 
b) 
c) 
d) 
e) 
f)

DOSE BUTTON FOR A DRUG DELIVERY DEVICE AND METHOD FOR MANUFACTURING A DOSE BUTTON

CROSS REFERENCE TO RELATED APPLICATIONS

The present application is a 35 U.S.C. 371 National Application of PCT/EP2010/054352 filed Mar. 31, 2010, which claims priority to European Patent Application No. 09004674.9, filed Mar. 31, 2009 and U.S. Provisional Patent Application No. 61/169,880, filed Apr. 16, 2009, the entire contents of which are incorporated entirely herein by reference.

The present invention relates to a dose button for a drug delivery device. Furthermore, the present invention relates to a method for manufacturing a dose button.

Drug delivery devices are generally known for the administration of a drug, for example insulin, but also for other medicinal products for self-administration by a patient. Because of the daily necessity to use this drug delivery device there are ambitions to make the use of these drug delivery devices more comfortable and safer for the user. Mostly the drug delivery devices are pen-type injectors wherein a pre-set dose of the drug can be injected. Some examples are described in the document EP 1 923 085 A1 and EP 0 554 995 A1.

In some cases it is necessary for a patient to use two different types of insulin or two different drugs. Then it is helpful for the patient to have one pen for one type of insulin and another pen for the other type. To avoid a mix-up the two insulin types, it is necessary to make the pens distinguishable.

It is an object to the present invention to provide a drug delivery device comprising a dose button which helps the user in operating a drug delivery device.

According to a first aspect of the present invention, a dose button for a drug delivery device is provided. The dose button may be manufactured by means of a cutting-off process. The dose button may be a metal dose button.

In this process the dose button is brought to a specific geometry by removing excess material using various kinds of tooling. If a plastic dose button should be used the way of manufacture one would be by injection molding. This manufacturing method has the disadvantage that the production process is very complex. To create plastic parts by injecting molding, it is necessary to produce a casting mold. Such casting molds are expensive to manufacture. Another disadvantage of injection molding is that it is not flexible in producing different surface styles.

In a preferred embodiment the surface structure of the dose button is milled or lathed.

Modern CNC lathes can perform a vast number of complex operations. They can also carry out secondary operations, like milling, by using driven tools. By using the data of a CAD database, it is possible to switch very quickly from one design to another.

According to one particularly preferred embodiment of the present invention, the material used for the dose button comprises metal.

There are a lot of possible varieties of this. The dose button can be coated with metal or can fully consist of metal. The material can be pure metal or an alloy. By using metal, there are some advantages which can be achieved, even if the material itself is more expensive than plastic. For instance it is more robust and easier to clean.

In one embodiment the metal used for the dose button is steel or aluminium. But it is also possible to use any other metal.

According to a further preferred embodiment, the surface of the dose button has a specific structure.

This structure is three-dimensional for the aim that the dose buttons have haptic differences distinguishable by the user. It is not sufficient to distinguish the two pens by means of visual features, but also by means of tactile features. This is needed because one of the effects of diabetes is that it can lead to severe visual loss or blindness.

In one embodiment the surface structure of the dose button is indicative of the drug to be contained in the drug delivery device.

By providing a three-dimensional surface structure of the dose button and the possibility of distinguishing two different drug delivery devices by the differences of the dose buttons, the user can distinguish two different insulin pens just by means of haptic features. Even for a user with impaired vision, it is possible to distinguish the pens by feeling the surface of the dose button.

In another embodiment the dose button is firmly connected with the drug delivery device.

By firmly connecting the dose button to the drug delivery device it is always possible to use the right pen for the right drug just by associating a special surface of the dose button with the contained drug.

In one embodiment the surface of the dose button forms a pattern.

The surface structure of the dose button may comprise one or more structural elements. The structural elements may form a pattern. In particular, structural elements may be grouped to form a pattern. There are a lot of different possible patterns like circles, crosses or bumps or even more intricate patterns. Every surface structure is possible which can be recognized by haptic perception.

In another preferred embodiment the surface of the dose button is colored.

The dose button can be colored by the metal used to form the dose button, but can also be colored after the manufacturing process.

Another aspect relates to a drug delivery device which comprises the dose button. The drug delivery device comprising the dose button is preferably reusable.

In this case, it may be possible for the user to choose a drug delivery device containing a drug with a specific dose button and use this for a long time by exchanging the vial in the drug delivery device once the drug is exhausted. Therefore, it is possible to use the same pen for the same drug. The metal dose button used is long living and the surface of the metal dose button does not wear off so fast in comparison to a plastic material.

In one embodiment the dose button of the drug delivery device is pressed to inject a specific dose of the drug. In particular, pressing of the dose button may trigger a dose dispensing action.

By carrying out the necessary action of pressing the dose button to inject the drug, the user inevitably feels the surface of the dose button and it is possible for him to avoid using the wrong medicine.

According to an embodiment, the drug delivery device comprises the previously described dose button. The drug delivery device may comprise one, two, or more of a housing, a cartridge holder, a cartridge containing the drug, a label and a cap. One, two, or more of the housing, the cartridge holder, the cartridge, the label and the cap may comprise a respective surface structure. The respective surface structure may be substantially equivalent or identical with the surface structure of the dose button.

The substantially equivalent or identical surface structure may identify one type of drug held in the cartridge of the device. This may increase the user's confidence that he is administering the correct drug. Anytime during operation of the device, e.g. during setting and delivery of the dose and/or while preparing the device for operation, the user may view and/or contact at least one of the specific surface structures.

The substantially equivalent or identical surface structure may comprise an identical number and/or an identical shape of one, more or all structural elements which are grouped to form the surface structure. Preferably, said structural elements comprise a structural depth large enough to generate a tactile feedback when a user contacts the respective surface structure. The substantially equivalent or identical surface structure may comprise a different size and/or a different material of the structural elements. Though certain differences in size and/or material of the structural elements may be allowed, the respective surface structure is preferably adapted and arranged to provide the same information to the user, e.g. information about the device and, in particular, the drug held in the cartridge of the device.

In one embodiment a set of at least two drug delivery devices comprising a dose button is provided, wherein each drug delivery device in the set is distinguishable from the others by a characteristic surface structure of its dose button.

In the set, there are different surface structures on every pen. If one needs to use for example two different types of insulin, maybe short-acting and long-acting insulin, one just needs to get the set and it is possible to distinguish the two drug delivery devices by the characteristic surface of the dose button.

It might be possible that the different pens just can be used with a special kind of vial and therefore with a special kind of drug. Then it is an advantage of the present invention that the user is prevented from inserting the wrong vial in a pen.

In another preferred embodiment a set of at least two drug delivery devices is provided. Every drug delivery device may carry a cartridge with a different drug.

If the user needs for example two types of insulin it is possible to buy these two types together with the fitting drug delivery devices. Furthermore, these two devices preferably comprise distinguishable dose buttons.

According to an embodiment, the previously described set of at least two drug delivery devices is provided. The respective drug delivery device may comprise one, two, or all of the following components: A cap for the drug delivery device, a cartridge holder for the drug delivery device, a cartridge for the drug delivery device, a housing for the drug delivery device and a label for the drug delivery device. One, two, more or all of the components may comprise a surface structure. The surface structure may be substantially equivalent or identical for the components of the respective device. Components of different devices may comprise different surface structures.

Components with different surface structures may be part of devices holding different drugs.

The components mentioned above may be assembled to form one single drug delivery device. In particular, components of one predetermined device may comprise the substantially equivalent or identical surface structure.

The at least two different drug delivery devices may be customized to the drug to be delivered by providing components with different surface structures. A specific surface structure may be chosen for all components of one of the devices which are provided with the surface structure. A different surface structure may be provided for the components of an other device. In particular, the different surface structures may be adapted to identify the drug held in the respective device.

The user may choose one first device and, thus, one first drug, he wants to use by viewing and/or contacting the surface structure on the components of the first device. The user may contact and/or move one component of said first device with respect to the main housing, e.g. for preparing the first device for operation. Afterwards, the user may put the first device aside, e.g. for preparing a second device providing components with a different surface structure which identifies a second drug held in the second device, for operation. Later on, when the user wants to dispense the first drug, the user grabs one of the two devices previously prepared for operation. By means of the surface structure provided on the components of said device, the user can verify at once, whether he has grabbed the right device, i.e. the first device holding the first the drug. Hence, provision of a device providing high safety for the user is facilitated.

According to a preferred embodiment, a dose button for a drug delivery device is provided which is manufactured by means of a cutting-off process.

The dose button may comprise a surface structure, in particular a tactile marking. In particular, due to said manufacturing process, the dose button may comprise a specific surface structure which is adapted to identify a drug held in a cartridge of the device.

According to a preferred embodiment, a method for manufacturing a dose button for use in a drug delivery device is provided, the dose button comprising a metal, wherein the method comprises the step of a cutting-off-process.

In a first manufacturing step, a metal work piece may be provided. In a second manufacturing step, material may be cut-off from a surface of the work piece. The material may be cut-off such that, at the end of the manufacturing process, the surface comprises a surface structure. The surface structure may be formed by cutting -off material which laterally surrounds the desired position of a desired surface structure but which is not required for forming the desired surface structure.

Figure 2:
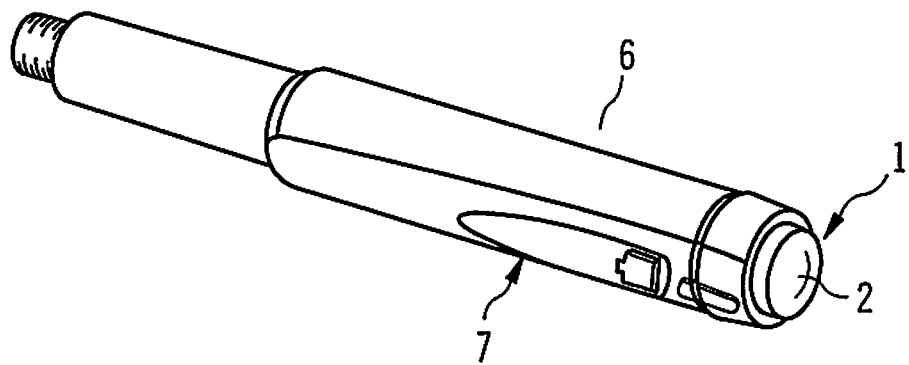
Figure 3:
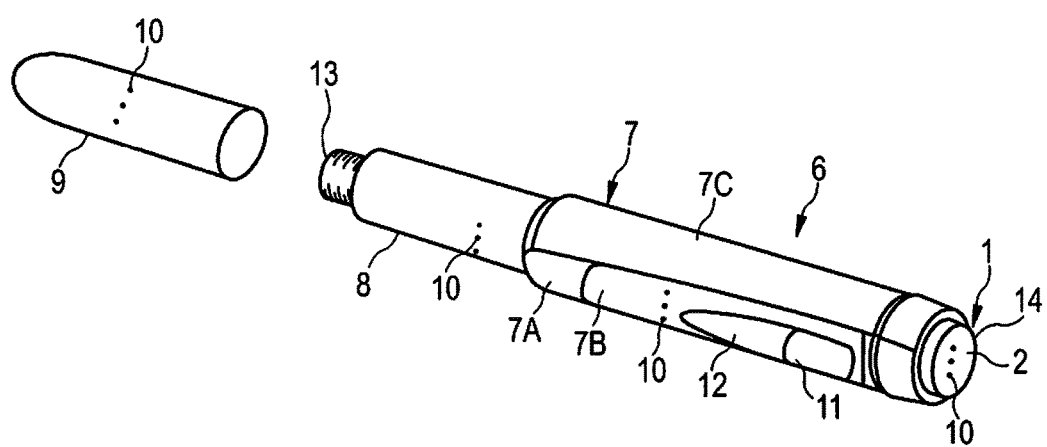

In the following the invention is described in further details with references to the drawings, wherein FIG. 1 shows a cross sectional view and a top view of a three possible dose buttons according to the invention, FIG. 2 shows a drug delivery device comprising a dose button according to the invention, and FIG. 3 shows a further exemplary embodiment of a drug delivery device.

Some preferred embodiments of a dose button 1 according to the present invention will now be discussed with reference to FIGS. 1 to 3. Identical reference signs denote identical or comparable components.

FIG. 1a shows a cross sectional view of a dose button 1. The dose button may consist of metal. Particularly, the dose button 1 may be a metal dose button. According to the embodiment shown, the surface structure of the dose button 1 shows a bump 3. The bump 3 is arranged in the middle of the surface 2 which may be rounded down to prevent that the user of the drug delivery device 6 gets hurt while using it. The surface structure was milled or lathed by using a CNC lathe.

FIG. 1b is a top view of the same dose button 1 as described in FIG. 1a.

In FIG. 1c a cross sectional view of another surface structure of a dose button 1 is shown. In this case there are two circle shaped protrusions on the surface 4, 41 with plain surface between the protrusions. One has a larger radius than the other. The outer circle 4 and the inner circle 41 are concentric. For a better view, a top view of this structure is shown in FIG. 1*d*.

In FIG. 1*e* a cross sectional view is shown of a surface structure with a plurality of bumps 5 distributed over the surface. Apart from these bumps 5 a plain surface is shown. By taking a look at the top, as it is shown in FIG. 1*f*, one can see that the bumps 5 form a vertical and horizontal line. These lines intersect at the middle of the surface 2 of the dose button 1.

In FIG. 2 a drug delivery device 6 is shown. The device 6 comprises a housing 7. The drug delivery device 6 and the housing 7 have a distal end and a proximal end. The term "distal end" designates that end of the drug delivery device 6 or a component thereof which is or is to be arranged closest to a dispensing end of the drug delivery device 6. The term "proximal end" designates that end of the device 6 or a component thereof which is or is to be arranged furthest away from the dispensing end of the device 6.

The device 6 comprises a dose button 1. The dose button may be arranged on the proximal end of the housing 7. The dose button 1 can be depressed by a user for delivering a pre-set dose of a drug. The drug may be held in a cartridge of the device 6 (not explicitly shown). The term "drug", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, a antibody, an enzyme, an antibody, a hormone or an oligonucleotide, or a mixture of the above-mentioned pharmaceutically active compound.

In a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis.

In a further embodiment the pharmaceutically active compound comprises at least one peptide for the treatment and/or prophylaxis of diabetes mellitus or complications associated with diabetes mellitus such as diabetic retinopathy.

In a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

As already explained in connection with FIGS. 1a to 1f, the surface 2 of the dose button 1 can have any possible structure, including visual, e.g. colour, and haptic features. The surface structure may identify one predetermined drug held in the cartridge of the device 6.

On the basis of different colours and/or different tactile structures on the surface 2 of the dose button 1, it may be possible for a user to distinguish between different devices 6, in particular devices 6 holding different drugs. Therefore, the user knows which drug delivery device 6 he has to operate just by feeling and/or seeing the respective dose button 1, in particular the surface structure of the respective dose button 1.

FIG. 3 shows a further exemplary embodiment of a drug delivery device.

The drug delivery device 6 comprises the previously mentioned housing 7. The housing 7 comprises a housing body 7A. The drug delivery device 6 comprises a cartridge holder 8. The cartridge holder 8 is permanently or releasably connected to the housing body 7A to form the housing 7 of the device 6. Preferably, the cartridge holder 8 is releasably connected, for example screwed, to the housing body 7A to allow for introducing a replacement cartridge into the device 6.

The drug delivery device 6 comprises a housing insert 7B. The housing insert 7B is part of the housing 7 of the device 6. The housing insert 7B is inserted into and, permanently or releasably, connected to the housing body 7A. Preferably, the housing insert 7B is releasably connected, for example snap-fitted, to the housing body 7A to allow insertion of a replacement housing insert 7B into the housing body 7A. The housing insert 7B is preferably arranged in a recessed section of the housing body 7A (not explicitly shown). Thus, the housing insert 7B does not significantly increase the radial extension of the device 6. Preferably, the housing insert 7B ends flush with the housing body 7A on an outer surface of the housing 7.

The housing insert 7B comprises a window section 11. The window section 11 is arranged in the proximal end section of the housing insert 7B. The window section 11 comprises a transparent or translucent window. The window may enable the user to view through the housing insert 7B. Preferably, the housing body 7A comprises an aperture with which the window section 11 overlaps. Thus, the user may view in the window section 11 through the housing 7 to a component housed therein, e.g. to members of a drive mechanism retained in the housing 7.

The housing insert 7B comprises a label section. The label section is arranged distally offset from the window section 11. The label section is configured for holding a label 12. The label 12 may be releasably or permanently attached to the label section. Preferably, the label 12 is releasably attached to the label section.

The housing 7 comprises an outer lateral surface 7C. The outer lateral surface 7C connects a distal end-face 13 of the drug delivery device 6, e.g. a distal end of the cartridge holder 8, and a proximal end-face 14 of the drug delivery device 6, e.g. the surface 2 of the dose button 1, with one another.

The device 6 comprises the previously mentioned cartridge (not explicitly shown). The cartridge is retained in the cartridge holder 8. The cartridge holder 8 stabilizes the cartridge mechanically. The cartridge may hold a plurality of doses of the drug.

The device 6 comprises the previously described dose button 1. The dose button 1 comprises the surface 2, in particular an actuation surface. The surface 2 forms the proximal end-face 14 of the device 6. The user may contact the surface 2 and, hence, the previously described structure on the surface 2, when dispensing the set dose.

The drug delivery device 6 may be an injection device. The drug delivery device 6 may be a pen-type device, in particular a pen-type injector. The device 6 may be a disposable or a re-usable device. The device 6 may be configured to dispense fixed doses of the drug, in particular doses which may not be varied by the user, or variable, preferably user-settable, doses of the drug. The drug delivery device 6 may be a manually, in particular a non-electrically, driven device.

The drug delivery device 6 comprises a cap 9. The cap 9 is connectable to the housing 7. In particular, the cap 9 is securable to the distal end of the housing body 7A. In a storage mode of the device 6, the cap 9 is adapted and arranged to cover the dispensing end of the drug delivery device 6. The cap 9 is configured to cover the cartridge holder 8. For preparing the device 6 for operation and, in particular, for bringing the device into an operational mode, e.g. a mode which allows for setting and delivering drug, the cap 9 is unsecured from the housing body 7A to uncover the cartridge holder 8.

The dose button 1 comprises the surface structure 10 as described in connection with FIGS. 1a to 1f and 2. The surface structure 10 of the dose button 1 identifies one predetermined drug held in the cartridge 8 of the device 6. According to the embodiment shown in FIG. 3, the surface structure 10 comprises a tactile marking. Tactile markings may be especially suited for users with impaired vision, e.g. users suffering from diabetes. Additionally or alternatively, the surface structure 10 may comprise a colour marking.

In addition to the surface structure 10 of the dose button 1, the housing 7, in particular the housing insert 7B, may comprise a surface structure 10. An additional surface structure 10 may be provided on the cap 9. An additional surface structure 10 may be provided on the cartridge holder 8 and/or the cartridge. An additional surface structure 10 may be provided on the label 12.

The surface structure 10 of the dose button 1, the cartridge holder 8, the cartridge, the cap 9 and the label 12 may be substantially equivalent or identical, e.g. the surface structure 10 may comprise substantially equivalent or identical tactile markings as shown in FIG. 3. In particular, the respective surface structure 10 may comprise the same shape and/or alignment of the structural elements with respect to each other. However, the respective surface structure 10 may comprise a different size and/or material. The respective surface structure 10 is adapted to generate a similar, preferably the same, tactile and/or visual feedback within the user. In particular, the surface structure 10 may provide the same information to the user. In particular, the surface structure 10 is adapted and arranged to signal the user which device the user is operating and, in particular, which drug is actually set and dispensed during operation of the device 6. One set of substantially equivalent or identical surface structures 10 preferably identifies one predetermined device 6 and, hence, one predetermined drug held in the cartridge of said device 6.

The respective surface structure 10 is provided on the outer surface of the respective component, e.g. the surface 2 of the dose button 1, the outer surface of the cap 9, the outer surface of the cartridge, the outer surface of the cartridge holder 8 and/or the outer (lateral) surface 7C of the housing 7, in particular of the housing insert 7B. In this way, the user can easily contact the surface structure 10 when he holds the device 6 when preparing the device 6 for operation and/or when setting and/or when delivering a dose of the drug.

The surface structure 10 may help to distinguish two or more different devices 6 holding different drugs from each other. These drug delivery devices 6 may comprise a similar exterior shape. Furthermore, the different drug delivery devices 6 may comprise a similar colour. The different drug delivery devices 6 may be adapted to hold different drugs. Due to the similar exterior shape and/or colour, a user may easily mix-up the different drug delivery devices 6 if the devices are not marked differently, e.g. by different surface structures. This may have fatal or even lethal consequences to the user.

However, the surface structure 10 of the components of one of the devices 6 may be different from the surface structure 10 of the components of any other of the device 6. In particular, the surface structure 10 may be different for different drugs held in the cartridge of the respective device 6. Accordingly, by means of the surface structure 10, the user may easily distinguish between the different drugs and, hence, between the different drug delivery devices 6. In particular, upon viewing and/or contacting the surface structure 10, the user may realize immediately which device 6 he is operating or intending to operate and, in particular, which drug is held in the cartridge of the respective device 6.

The present examples and embodiments are to be considered as illustrative and not restrictive, and the invention is not to be limited to the details given herein, but may be modified within the scope and equivalence of the appended claims.

REFERENCE NUMERALS

1 Dose button
2 Surface of the dose button
3 Bump
4 Outer circle
4 Inner circle
5 Bump
6 Drug delivery device
7 Housing
7A Housing body
7B Housing insert
7C Outer lateral surface
8 Cartridge holder
9 Cap
10 Structure
11 Window section
12 Label
13 Distal end-face
14 Proximal end-face

The invention claimed is:

1. A drug delivery device comprising:
exactly one dose button having a tactile feature on a surface of the dose button, the tactile feature being indicative of a drug to be delivered by the drug delivery device, wherein the surface of the dose button comprises a metal having one or more cutting marks formed by a cutting-off process, and wherein the tactile feature is formed by the cutting-off process such that the one or more cutting marks laterally surround the tactile feature on the surface of the dose button;
a housing comprising a housing body and a cartridge holder releasably attached to the housing body, wherein the cartridge holder is adapted to hold a cartridge containing the drug; and
a removable cap adapted to cover the cartridge holder,
wherein the housing body, the cap, and one or both of the cartridge holder and the cartridge each comprise a respective tactile feature substantially equivalent or identical to the tactile feature of the dose button.

2. The drug delivery device according to claim 1, wherein the drug delivery device further includes a label section permanently or releasably connected to the housing body, and wherein the label section comprises the respective tactile feature substantially equivalent or identical to the tactile feature of the dose button.

3. The drug delivery device according to claim 1, wherein the tactile feature comprises an inner circle-shaped protrusion and an outer circle-shaped protrusion, wherein the inner circle-shaped protrusion and the outer circle-shaped protrusion are concentric.

4. The drug delivery device according to claim 1, wherein the metal comprises a metal coating on the dose button.

5. The drug delivery device of claim 1, wherein the drug delivery device further comprises a housing insert permanently or releasably connected to the housing body, wherein the respective tactile feature is disposed on the housing insert.

6. Drug delivery device according to claim 1, wherein the cartridge holder and the cartridge each comprise the respective tactile feature substantially equivalent or identical to the tactile feature of the dose button of the respective device.

7. A set of at least two drug delivery devices each comprising:
a metal dose button manufactured by means of a cutting-off process and including a characteristic surface having a tactile feature that forms a pattern, the pattern of the tactile feature being indicative of a drug to be delivered by the respective drug delivery device,
wherein the tactile feature of each dose button is formed by a cutting-off process such that one or more cutting marks laterally surround the tactile feature on the characteristic surface of the dose button;
a housing comprising a housing body and a cartridge holder releasably attached to the housing body, wherein the cartridge holder is adapted to hold a cartridge containing the drug to be delivered by the respective drug delivery device; and
a removable cap adapted to cover the cartridge holder,
wherein every drug delivery device in the set is distinguishable from every other by the characteristic surface structure of its dose button,
wherein each respective drug delivery device is configured for delivery of a different drug,
wherein, for each drug delivery device, the housing body, the cap, and one or both of the cartridge holder and the cartridge each comprise a respective tactile feature, the respective tactile feature being substantially equivalent or identical to the tactile feature of the dose button of the respective device, and
wherein the tactile feature is different for each of the at least two drug delivery devices.

8. The set of at least two drug delivery devices according to claim 7, wherein each drug delivery device further includes the cartridge with the drug to be delivered by the respective drug delivery device.

9. The set of at least two drug delivery devices according to claim 7, wherein the at least two drug delivery devices are the same exterior color.

10. The drug delivery device according to claim 7, wherein each of the cartridge holder and the cartridge of each drug delivery device comprise the respective tactile feature substantially equivalent or identical to the tactile feature of the dose button of the respective device.

11. A drug delivery device comprising:
exactly one dose button;
a housing comprising a housing body and a cartridge holder releasably attached to the housing body, wherein the cartridge holder is adapted to hold a cartridge containing a drug; and
a removable cap adapted to cover the cartridge holder,
wherein a surface of the dose button has a specific structure forming a tactile marking that is indicative of the drug contained within the cartridge held by the cartridge holder of the drug delivery device,
wherein the surface of the dose button further comprises one or more cutting marks from a cutting-off process,
wherein the tactile marking of each dose button is formed by the cutting-off process such that the one or more cutting marks laterally surround the tactile feature on the surface of the dose button, and
wherein the housing body, the cap, and one or both of the cartridge holder and the cartridge each comprise a respective tactile feature substantially equivalent or identical to the tactile feature of the dose button.

12. The drug delivery device according to claim 11, wherein the surface and the tactile feature of the exactly one dose button comprise a metal.

13. The drug delivery device according to claim 11, wherein the surface of the exactly one dose button comprises a metal coating.

14. The drug delivery device according to claim 11, wherein the cartridge holder and the cartridge each comprise the respective tactile feature substantially equivalent or identical to the tactile feature of the dose button of the respective device.

* * * * *